United States Patent [19]

Benoit et al.

[11] 4,139,011

[45] Feb. 13, 1979

[54] DEVICE FOR DRIVING A NEEDLE INTO A PATIENT

[76] Inventors: Jean L. P. M. Benoit, 74, rue du Fort Saint-Irenee, Lyon, France, 69005; Frank Z. Warren, 446 E. 88th St., New York, N.Y. 10028

[21] Appl. No.: 751,879

[22] Filed: Dec. 17, 1976

[30] Foreign Application Priority Data

Dec. 19, 1975 [FR] France .............................. 75 39781
May 19, 1976 [FR] France .............................. 76 15862

[51] Int. Cl.² ............................................ A61B 17/34
[52] U.S. Cl. ............................ 128/329 R; 128/329 A
[58] Field of Search ......... 128/2.06 E, 2.1 E, 303.18, 128/329 A, 329 R, 330, 418, 419 P; 124/41 R

[56] References Cited

U.S. PATENT DOCUMENTS

| 8,843 | 3/1852 | Sounenburg et al. ...... 128/303.18 X |
|---|---|---|
| 1,175,035 | 3/1916 | Wooster ........................ 124/41 R X |
| 3,030,959 | 4/1962 | Grunert ............................... 128/329 |
| 3,090,151 | 5/1963 | Stewart et al. ................ 124/41 R X |
| 3,208,452 | 9/1965 | Stern .............................. 128/329 UX |
| 3,943,935 | 3/1976 | Cameron ............................. 128/330 |

*Primary Examiner*—Robert W. Michell
*Assistant Examiner*—Michael H. Thaler
*Attorney, Agent, or Firm*—Dowell & Dowell

[57] ABSTRACT

A device for driving a needle into the tissues of a patient, the needle being a dart-like point attached by a shank to a head, and the device including a body having a bore therethrough, the needle occupying a zone of the bore near its outlet, a sliding pusher member in the bore having a split at one end to grip the head of the needle, the bore being shaped to compress the split end on the head of the needle when the pusher member is retracted, and to release the grip when the pusher member is advanced, and an actuator to advance the pusher member through a stroke of limited length.

7 Claims, 15 Drawing Figures

DEVICE FOR DRIVING A NEEDLE INTO A PATIENT

FIELD OF INVENTION

This invention relates to medical devices for driving a needle through the skin of a patient, and more particularly relates to single use throw-away devices made of molded plastic and containing a needle which is injected under the skin and remains therein after the needle driving device is removed.

BACKGROUND OF INVENTION

It is known practice in connection with certain medical treatments to drive a needle having one of a number of different shapes into the body of a patient, the needle being generally shaped in the form of a skin penetrating dart. It is also known sometimes to use such needles in place of electrodes for the purpose of administering treatments by electrical currents.

The insertion by hand of a needle of the type in question requires considerable skill, and moreover, it involves more than negligable risk of infection at the point of insertion in spite of care exercised in sterilizing the needles themselves and the hands of the operator.

THE INVENTION

The invention seeks to remedy this problem and to provide an improved embodiment making it possible to drive a needle in a semi-automatic manner without any risk of infection.

The embodiments of the invention essentially comprise:
 a hollow body suitable to be applied against the skin of the patient at a point where the needle is to be introduced;
 a needle having a triangular tip and a flat head which before use is mounted in the interior of the body;
 a movable member in the interior of the body and having means for supporting the needle; and
 means associated with the body and operative to actuate the movable member for the purpose of projecting the needle out of the body.

The means for driving the needle may comprise a spring associated with a locking means for retaining the system retracted until the moment of use, or it may be a simple pusher means manually operated and preferably combined with a suitable device for creating a dragging counter force which suddenly releases to assure a kind of snap action which consequently provides an unrestrained and rapid driving of the needle.

The needle may simply be guided, in a shaped bore within the hollow body in which it is inserted, by a pusher member which is made one piece with the slide member supporting the needle. Moreover, it is also possible to provide a pusher member having a portion designed to receive the needle in a suitable holder provided in its extreme end, and to retain the needle up to the moment when it is injected into the skin of the patient. In one form of construction of the pusher, it is split at its bottom to receive the head of the needle in the split by spreading it a little bit, whereby a small pressure provided by the bore against the sidewall of the sliding member tends to reclose the split and thereby assure that the needle will be retained despite its weight, and vibrations or shocks. The bore includes an outlet which is somewhat flared in a manner such that once the needle has been projected, there is no longer any retaining force except for the very slight tendency toward closing of the slit in the end of the slide member, whereby the head can at once disengage itself from the slide member without any difficulty.

All of these various forms of the invention are preferably made of molded plastic, so that the price of manufacture is so greatly reduced that it can be considered, even including the needle which it retains, as an apparatus which need be used only once. A suitable detent or locking means can be very simply supplied in the form of a lateral opening provided in the sidewall of the body and a cooperating tooth carried by a resiliently deformable arm which is formed in one piece with the movable slide member.

Figures 1, 6:
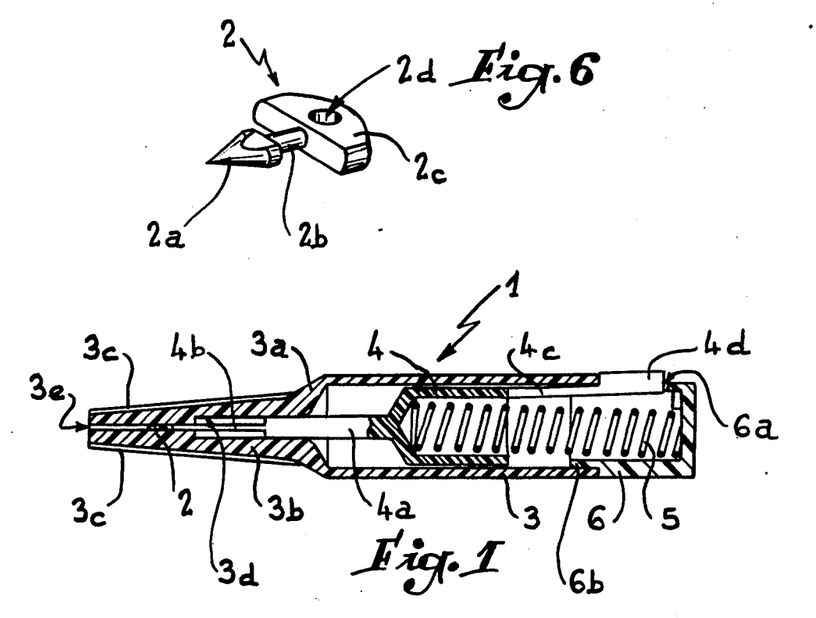
FIG. 1 is a cross-sectional longitudinal view through a first embodiment of the invention which is spring operated, the parts being illustrated in a retracted position.
FIG. 6 is a perspective view of a needle for use in the device.
Figure 2:
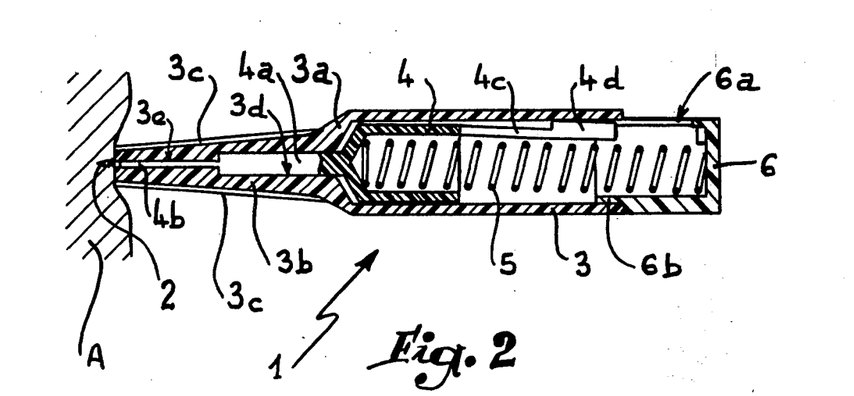
FIG. 2 is a sectional view similar to FIG. 1, but showing the apparatus in released position.
Figure 3:
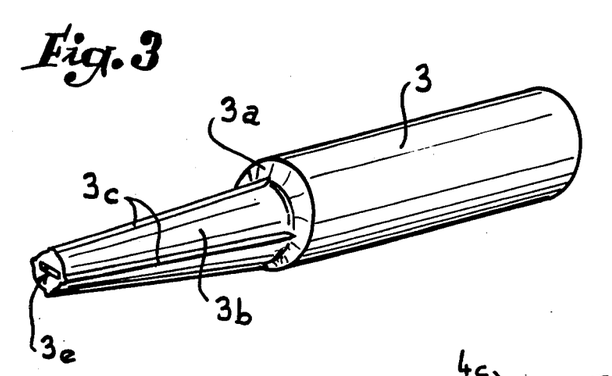
FIG. 3 is a perspective view of the outside body member of the device.

Referring now to the embodiment of FIGS. 1 through 6, the embodiment generally designated by the reference numeral 1 shows a device intended to drive a needle shown in FIG. 6 into the skin. This device comprises a cylindrical hollow body 3, one end of which is closed by an end member 3a which is integral with the body and takes the form of a truncated cone 3b on whose periphery there are provided four longitudinal ribs 3c intended to facilitate positioning of the device on the skin of a patient. See also FIG. 3. Within the hollow body 3 there is mounted a slide member 4, FIGS. 1 and 4, one end of which carries an integrally formed stem 4a having a cylindrical cross-section, which gives way to a flattened stem portion 4b. The cylindrical stem portion and the flattened stem portion are engaged within a bore provided axially through the head 3b of the body, the bore itself comprising a circular zone 3d followed by a flattened zone 3e, the latter terminating in an outlet at the extreme end of the head.

Figures 4, 5:
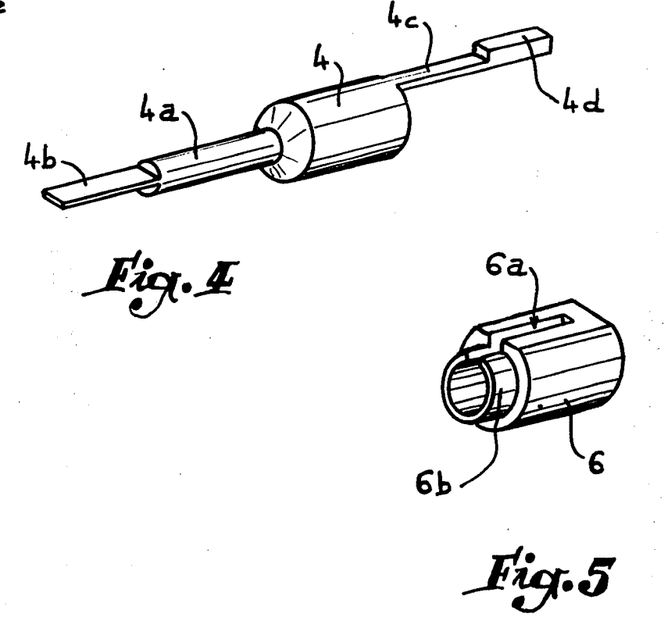
FIG. 4 is a perspective view of the slide member of the device.
FIG. 5 is a perspective view of the cap member which retains the slide member in the body.

The other end of the slide member 4 includes a spring receiving socket, and on one side of the open socket there is an integrally formed extension 4c taking the form of an arm of reduced width as shown in FIG. 4, the arm extending toward the rear and terminating in a tooth 4d, the latter projecting radially away from the axis of the slide member.

In the normal retracted position as shown in FIG. 1, the tooth lies against the end of the body 3 in the slot 6a.

The slide member 4 supports a compression spring 5 which lies in a socket in the body and is compressed against the opposite end of the body 3 closed by the cap 6. As shown in FIG. 5, the closed end comprises a cap having a slot 6a to receive the tooth 4d and form a locking means. The cap is fixed onto the body 3 in any appropriate manner, for example, by the expedient of an extension 6b which is cemented in the open end of the body 3.

The bore 3d extending into the head 3a is intended to receive a needle 2 as shown in FIG. 6, comprising a conical point 2a, a shank 2b, and a head 2c. As shown, the head 2c has an uncurved cross-section whose thickness can be somewhat greater than the diameter of the shank 2b and the thickness of the conical point 2a, which is itself flattened on two surfaces parallel to the axis of the needle and parallel with the opposite faces of the head 2c. However, the point 2a can be flattened to present the same thickness as the head 2c itself, and coplanar therewith.

As an alternative variation, the needle 2 can be made by simply punching it from thin sheet metal, in which case its thickness would be constant throughout its length.

In whatever way the needle 2 is made, its dimensions are such that it can be entered by sliding into the flat portion 3e of the bore in the head 3b.

The device is advantageously made of molded plastic, of course with the exception of the spring 5 which is made of appropriate steel. As to the needle 2, it is preferably made of stainless steel or other metal which is not subject to corrosion and is compatible with animal organisms.

The first embodiment functions as follows:

In the retracted position shown in FIG. 1, the tooth 4d of the locking means retains the slide member 4 holding the spring 5 in compressed condition, and opposing the action of the spring. The needle 2 is lodged in the flat portion 3e of the bore of the head 3d substantially in contact with the free end of the flattened stem 4b carried by the stem portion of the slide member. It is noted that this flattened portion 4d and the rounded portion of the stem 4a of which it is a continuation are obviously retracted within the correspondingly shaped portions of the bore in the head 3b.

To use the device, it is only necessary to apply the outlet end of the head 3d against the location on the skin of the patient where it is desired to inject the needle, and then press the tooth 4d and push it into the interior of the body 3. Thereupon, the spring 5 is freed and it actuates the slide member 4 forwardly, so that the flattened stem portion 4b of the slide member drives the needle 2 and makes it penetrate into the skin A of the patient, FIG. 2. As is shown, at the end of the stroke of the slide member 4 the flattened stem portion 4b has been limited in its motion so that it stops short of being extended from the bore in the head 3b, whereby the head 2c of the needle 2 stops within the flat portion 3e of the aforesaid bore, and does not risk being itself forced into the skin tissue of the patient.

Thus, as mentioned above, it is possible to provide at a low price of manufacture a needle driving device 1 made of molded plastic providing a combined assembly which need be used only once. This device is therefore sold already charged with a needle and enclosed in a suitable sterilized sealed envelope which is not opened until the instant of injection, whereby all risk of infection is avoided.

The device can be used to achieve treatments of the type including the insertion of darts for acupuncture purposes under the skin, but it can also be used when it is desired to treat a patient by electrical currents, the needle serving then as an electrode. In this case, the head 2c may advantageously be provided with a hole 2d appropriate to receive a suitable electrical conductor.

Figure 7:
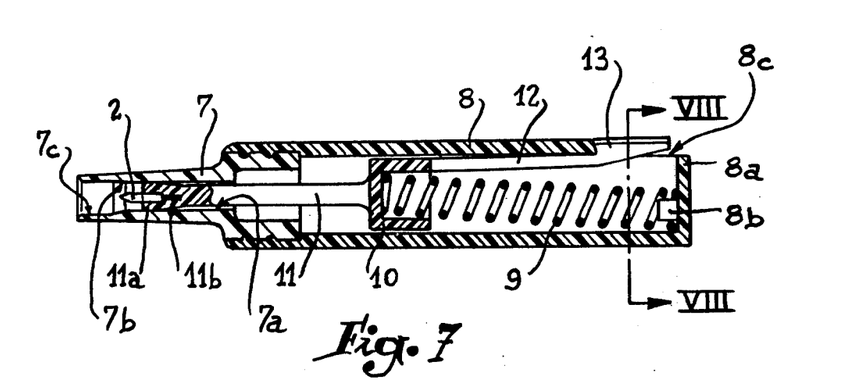
FIG. 7 is a cross-sectional longitudinal view taken through a second form of the invention.
Figure 8:
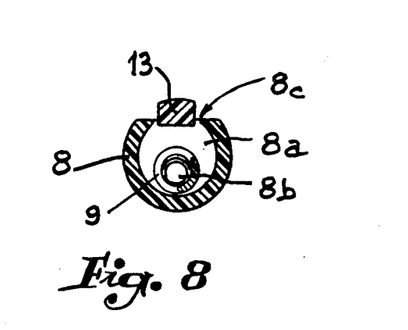
FIG. 8 is a transverse sectional view taken along line VIII—VIII of FIG. 7.
Figure 9:
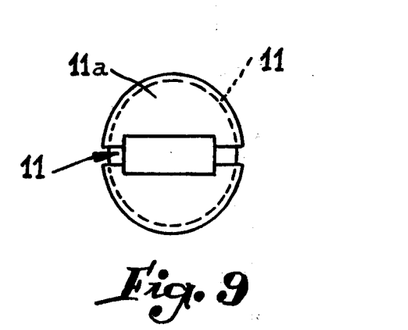
FIG. 9 is an enlarged view of the needle-pushing end of the slide member according to the second embodiment.

Referring now to the form of the invention shown in FIGS. 7 through 9, this second embodiment is distinguished from the preceding embodiment in that the head bearing the reference numeral 7 constitutes a separate piece from the cylindrical body 8 and is attached thereto by screwing or snapping into the body 8, whereby the opposite end of the body including the parts 7 and 8 is closed by an end wall 8a molded with the part 8 and including an interior boss 8b to center the spring 9. Of course, these modifications provide a structure which is substantially equivalent to the preceding form of the invention.

In this embodiment the slide member 10 is integral with a sliding pusher member 11 which is essentially cylindrical except for the portion toward its free end 11a where the diameter is slightly enlarged. The extreme end 11a present a cross-section which is slightly elliptical. It is split to provide a transverse slot 11b as shown in FIG. 9 which is disposed to follow the smaller cross-sectional axis of the ellipse, and which gives to the part a certain yieldable characteristic. It can thus provide a slight rubbing drag when it slides in a narrower cylindrical bore 7b whose diameter is slightly less than the ellipse as measured along its larger cross-sectional axis. The needle is placed freely within the bore and oriented to extend into the slot and can be maintained therein by protrusions providing a slight retaining grip on it. The sliding pusher member 11 is thus free to slide within the axial bore of the head 7, the bore comprising a narrower first zone 7a having an elongated cylindrical cross-section, followed by a flared zone 7b, which in turn is followed by an enlarged cylindrical zone 7c of greater diameter than the portion 7a. The narrower zone which constitutes the zone 7a has its diameter selected such that the end 11a of the sliding pusher member can pass therethrough only by exerting a small amount of force, but not sufficient to block the driving action of the spring 9.

The sliding member 10 is integrally provided with a resilient arm 12 oriented to the rear thereof and carrying a retaining tooth 13, the latter latching in an opening 8c in the lateral sidewall of the cylindrical portion 8 to form a releasable locking device.

In the retracted position of the device, the needle 2 is retained in position in the slot 11b as a result of contraction at the zone 7a imposed by the bore in the head 7 on the split end 11a. When the tooth 13 is released, the spring 9, provided with sufficient pressure, presses the sliding pusher member 10 and 11 rapidly outwardly in such a manner that the needle is forced into the skin of the patient. It is noted that at the beginning, its movement is dragged by the zone 7a of the bore, but as soon as the extremity 11a arrives in the zone 7c of the bore, the drag ceases and the movement can freely accelerate. Moreover, the needle is no longer retained because the spacing increases between the lips of the slot 11b in the bore zone 7c, and as a result the injecting device can be spaced from the body of the patient without the needle being guided in any appreciable fashion.

The advantage of the embodiment of FIGS. 7 through 9 is that the retention of the needle in the interior of the head 7 is completely assured and there is no risk whatever that the needle will become disengaged prematurely as a result of rough handling, vibration, shock, etc.

Figure 10:
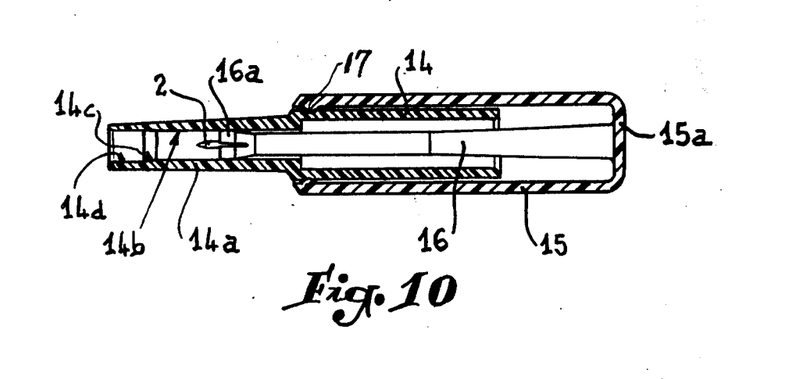
FIG. 10 is a longitudinal cross-sectional view showing a third form of the invention suitable for manual actuation.

Referring now to the embodiment of the invention illustrated in FIG. 10, the body referred to by the reference character 14 is made integrally with the head portion 14a. Over the body 14 an elongated cap 15 is slid into position, the transverse cross-section of the cap 15 being, for instance, cylindrical, or some other suitable configuration, for example, hexagonal. The end 15a of the cap is integrally formed with a slide member 16 having an outer end formed exactly like that shown in the embodiment of FIGS. 7 through 9, that is to say, with a split extreme end 16a of slightly increased diameter. The head 14a is also essentially similar to the head 7 of FIG. 7 and includes a bore having three zones, namely, a zone 14b of cylindrical profile, a zone 14c of flared profile, and a zone 14d of larger cylindrical diameter.

In this embodiment, the driving of te needle 2 is achieved by manual pressure on the cap 15, and is not automatically provided by a spring. Moreover, in this simplified form of the invention, the narrowed zone 14b of the bore through the body 14 provides a sort of trip-action whereby the drag which it provides requires a certain effort on the part of the operator to overcome, whereby when the drag action suddenly ceases, the manual effort exerted ends in a sharp acceleration and rapid penetration of the needle.

In the normal unused position, the slight contraction of the extremity 16a by the zone 14b of the bore suffices to retain the pusher 16 and the cap 15 in place. However, it is also possible to provide for this purpose a suitable detent system 17 if desired.

Figures 11, 13, 14:
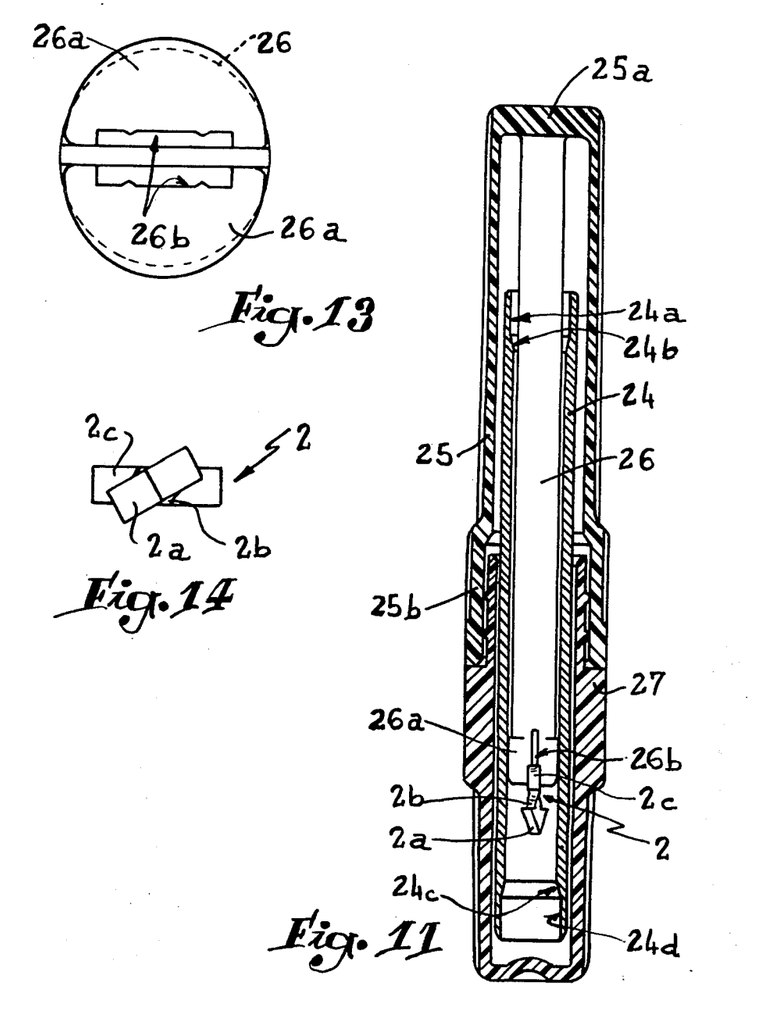
FIG. 11 is a longitudinal cross-sectional view taken through a fourth embodiment of the invention.
FIG. 13 is an enlarged end view showing the needle-pushing end of the slide member.
FIG. 14 is an end view of a modified form of the needle.

In the embodiment of the invention as shown in FIGS. 11 through 15, the body 24 is reduced to the form of a simple tube having identical extremities, comprising at one end the zones 24a and 24b, and at the other ends the zones 24c and 24d which permit the freeing of the needle 2 from the extremity 26a of the sliding pusher member 26. It is additionally provided with a protective cover 27 which engages in the enlarged open end 25b of a cap 25. It is also to be noted that the needle 2 is not flat, the plane of its head 2c being somewhat twisted with respect to the plane of its triangular point 2a as shown in FIG. 14.

Figure 12:
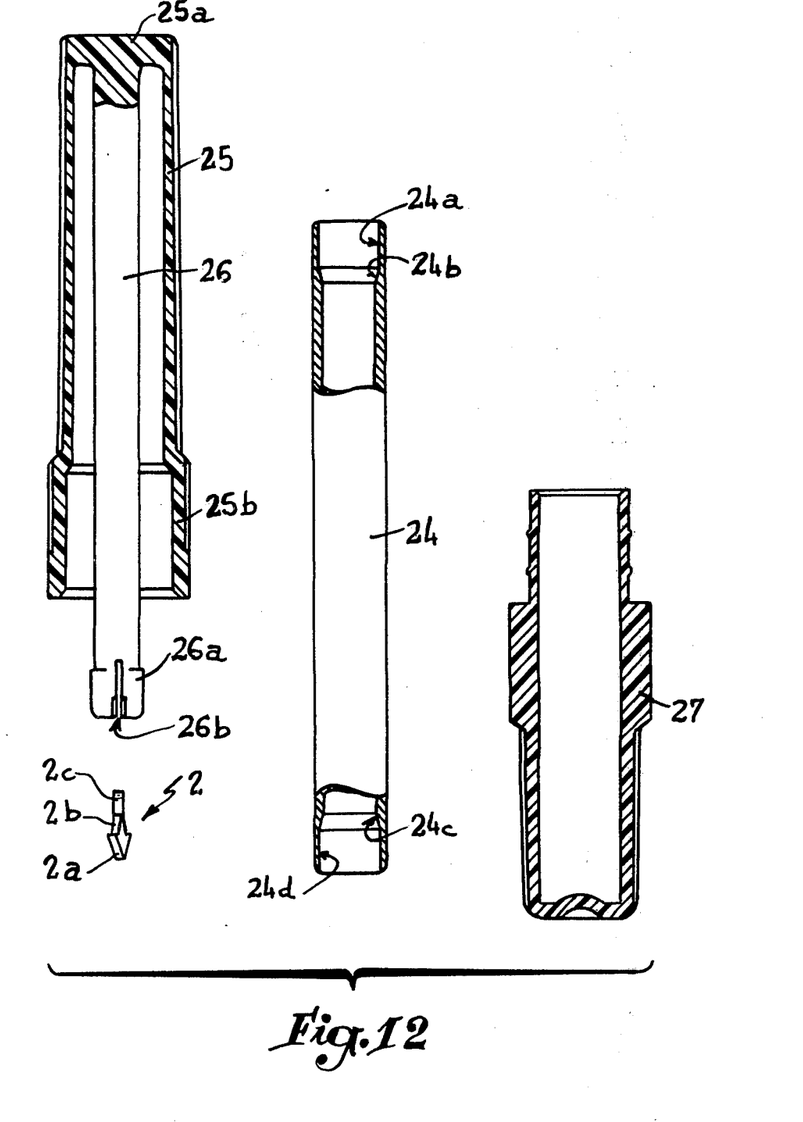
FIG. 12 is an exploded view showing the various parts of the fourth embodiment, illustrated partly in cross-section.
Figure 15:
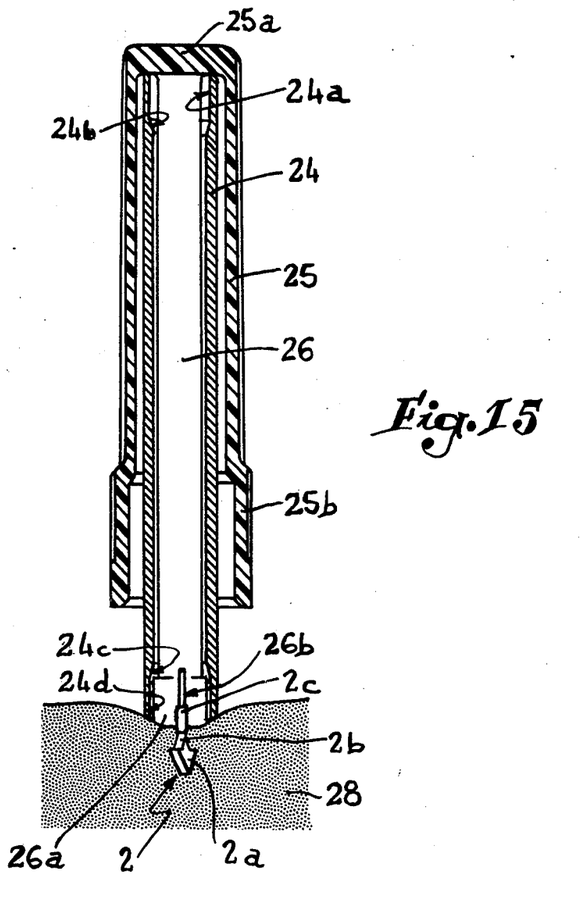
FIG. 15 is a longitudinal cross-sectional view of the fourth embodiment in the position which it occupies just after forcing the needle into the skin tissue of a patient.

During assembling of the device care must be taken not to force the pusher member 26 to the end of the tube 24 in such a manner that the split end 26a of the sliding pusher member leaves the zone of smaller diameter of the tube with the point of the needle passing outside thereof. At first, the tube 24 should be partially engaged upon the pusher member 26, then pushed further thereon using the protective cover 27 to position it in place thereon. It is noted that the tube 24 is symmetrical and that it can therefore be placed on the pusher 26 in any orientation.

The operation of the fourth embodiment of the invention as shown in FIGS. 11 through 15 is the same as that set forth above with reference to FIG. 10, except that before using the device it is obviously necessary to first remove the protective cover 27. In addition, it is noted that the reason for twisting the point of the needle with respect to its head is that the needle is then not in danger of being driven in an excessive manner into the skin of the patient, because its head cannot enter into the slit cut in the skin by the skewed point of the needle.

Of course, the needle shown in FIG. 14 is also equally usable in the embodiments of the invention shown in FIGS. 7 and 10.

We claim:

1. A device for driving a needle into the tissue of a patient, comprising:

a needle having a pointed tip and having a flat head joined to said tip;

a body having a bore extending thereinto and having an opening at the outlet end of the bore to be pressed against the tissue of the patient, the needle being inserted into the bore near said opening, and the bore having an enlarged zone with a closed end opposite said outlet end of the body;

a sliding pusher member in the bore behind the head of the needle and shaped to fit closely in the bore and slide therein, the sliding pusher member having an enlarged end in said enlarged zone of the bore and said sliding pusher member having at its other end a needle receiving slot shaped to receive the flat needle head, said other end being split at said slot and spread to receive and retain said flat head in the slot until the sliding pusher member is actuated to drive the needle, and the sliding pusher member being operative when actuated to drive the needle out of the bore into the tissue of the patient;

actuating means carried by the body and including a compression spring in said enlarged zone of the bore and engaging the enlarged end of the sliding pusher member, and means carried by the sliding pusher member and operative to engage the body and latch the pusher member in retracted position with the spring compressed, and releasable to free the spring to actuate the sliding member to drive the needle from the bore; and said bore having a narrowed zone spaced from said outlet and shaped to lightly compress the split end of the sliding pusher member to grip the head of the needle to retain it in the slot while the sliding pusher member is retracted with the split end thereof in said narrowed zone, and said bore having an enlarged zone joining said narrowed zone to said outlet, whereby the needle receiving end of the sliding member is released from gripping the head of the needle when the split end passes from the narrowed zone into the enlarged zone.

2. In a device as claimed in claim 1, the needle tip being joined to its head by a shank of cross sectional shape smaller than the tip or the head, and means to limit the stroke of the sliding member in the body so that at the end of the stroke only the tip of the needle and the shank extend beyond said opening and the head of the needle remains within the bore.

3. In a device as claimed in claim 1, the head of the needle being flat; the bore having a portion adjacent to said outlet which is flattened and shaped in cross-section to receive the head of the needle; and said sliding pusher member having a flat portion extending into said flattened portion of the bore behind the head of the needle.

4. In a device as set forth in claim 1, said body having a slot in its sidewall; and said latch means on the sliding pusher member comprising a resilient arm carrying a tooth disposed to enter the slot when the sliding member is retracted; and the tooth being manually disengageble from the slot from outside the body to release the locking means.

5. A device for driving a needle into the tissue of a patient, comprising:

a needle having a pointed tip and having a head joined to said tip;

a body having a bore extending therethrough and having an outlet end having an opening corresponding with one end of the bore to be pressed against the tissue of the patient, the head of the needle being inserted into the bore at said outlet end;

a sliding pusher member in the bore behind the head of the needle and operative when actuated to drive the needle out of the bore into the tissue of the patient;

actuating means carried by the body and operative to actuate the sliding member to drive the needle from the bore, said actuating means comprising a cap slidably mounted on said body at the opposite end from said opening and having a closed end, and said sliding pusher member extending out of the bore at said opposite end and joining the closed end of said slidable cap, the cap when manually pushed actuating said sliding member; and the head of the needle being flat and said sliding pusher member having a needle receiving end which is split to provide a slot shaped to receive and retain the needle head, said bore having a narrowed zone spaced from its opening and shaped to lightly compress the split needle receiving end of the sliding member to grip the head of the needle and retain it in the slot while the split end of the sliding member is in said narrowed zone, said narrowed zone providing a frictional drag on the sliding member, and said bore having an enlarged zone joining said narrowed zone to said outlet, whereby the needle receiving end of the sliding member is released from gripping the head of the needle when the split end passes from the narrowed zone into the enlarged zone of the bore.

6. In a device as set forth in claim 5, detent means on the body and yieldably maintaining the sliding pusher member retracted, and requiring the exertion of manual effort to overcome the drag thereof and suddenly actuate the pusher member.

7. In a device as set forth in claim 5, said needle having an intermediate shank joining said tip with said head, the head and the tip being flat and the shank being narrow in comparison with the width of the head, and the needle being twisted about the shank so that the tip is out of coplanar orientation with the head.

* * * * *